(12) United States Patent
Kong

(10) Patent No.: US 11,174,421 B2
(45) Date of Patent: Nov. 16, 2021

(54) METOD FOR PREPARING MINERAL ORE POWDER USING VEGETABLE ORGANIC MATTERS AND MICROORGANISMS

(71) Applicant: Byung Seok Kong, Busan (KR)

(72) Inventor: Byung Seok Kong, Busan (KR)

(*) Notice: Subject to any disclaimer, the term of this patent is extended or adjusted under 35 U.S.C. 154(b) by 69 days.

(21) Appl. No.: 16/558,723

(22) Filed: Sep. 3, 2019

(65) Prior Publication Data

US 2020/0407614 A1    Dec. 31, 2020

(30) Foreign Application Priority Data

Jun. 28, 2019    (KR) .................... 10-2019-0077473

(51) Int. Cl.
*C09K 5/14*    (2006.01)
*C22B 1/14*    (2006.01)

(52) U.S. Cl.
CPC . *C09K 5/14* (2013.01); *C22B 1/14* (2013.01)

(58) Field of Classification Search
CPC .... C09K 5/14; C22B 1/14; C22B 1/16; C22B 1/18; C22B 1/22; C22B 1/24; C22B 1/2406; C22B 1/26; C22B 3/18; C05D 9/00; C05F 11/08; C05G 1/00; C05G 3/00; C04B 2103/0001
See application file for complete search history.

(56) References Cited

U.S. PATENT DOCUMENTS

| | | | | |
|---|---|---|---|---|
| 6,669,882 B2 * | 12/2003 | Seok | ........................ | C08K 3/34 264/140 |
| 2020/0214300 A1 * | 7/2020 | Lee | ........................ | A01N 59/00 |

FOREIGN PATENT DOCUMENTS

| | | | | | |
|---|---|---|---|---|---|
| CN | 106754514 | A | * | 5/2017 | |
| CN | 107056144 | A | * | 8/2017 | |
| KR | 100267461 | B1 | * | 10/2000 | |
| KR | 20070014663 | A | * | 2/2007 | |
| KR | 20100082502 | A | * | 7/2010 | |
| WO | WO-0071206 | A1 | * | 11/2000 | .......... A61N 5/1029 |

OTHER PUBLICATIONS

English language machine translation of Moon (KR 20070014663 A) (Year: 2007).*
English language machine translation of Zhong (CN 106754514 A) (Year: 2017).*

(Continued)

*Primary Examiner* — Matthew R Diaz
(74) *Attorney, Agent, or Firm* — STIP Law Group, LLC

(57) ABSTRACT

The present invention provides a method for preparing mineral ore powder using vegetable organic matter and microorganisms. The method comprises a step of pulverizing seven minerals consisting of 20 wt % of zeolite, 20 wt % of hornblende, 10 wt % of elvan, 10 wt % of illite, 10 wt % of biotite, 20 wt % of tourmaline, and 10% of white clay into 325 mesh; a step of discharging impurities by heating the pulverized mineral powder at a temperature of 1,100° C. for a few days; a step of preparing a mineral ore powder by adding microorganisms and pulverized vegetable organic matter consisting of 30 wt % of mulberry bark, 25 wt % of pine needles, 20 wt % of cypress, 15 wt % of ginger plant, and 10 wt % of bush clover; and a step of drying the mineral ore powder at a temperature of 30° C. for 2 days to activate the microorganisms.

3 Claims, 2 Drawing Sheets

(56) References Cited

OTHER PUBLICATIONS

English language machine translation of Cho (KR 100267461 B1) (Year: 2000).*
English language machine translation of Yhun et al. (KR 20100082502 A) (Year: 2010).*
English language machine translation of Shi et al. (CN 107056144 A). (Year: 2017).*
English language machine translation of Nagasawa (WO 00/71206 A1) (Year: 2000).*

* cited by examiner

METOD FOR PREPARING MINERAL ORE POWDER USING VEGETABLE ORGANIC MATTERS AND MICROORGANISMS

CROSS-REFERENCE TO RELATED APPLICATIONS

This application claims the priority of the Korean Patent Applications NO. 10-2019-0077473 filed on Jun. 28, 2019, in the Korean Intellectual Property Office, the disclosure of which is incorporated herein by reference.

FIELD OF THE INVENTION

The present invention relates to a method for preparing mineral ore powder using vegetable organic matters and microorganisms, particularly a method for preparing mineral ore powder by heating and pulverizing seven (7) minerals that are beneficial to the human body but contain toxins and impurities at high temperatures in a furnace, removing toxin gases and impurities through carbonization, and drying the minerals for two days with liquid or powdered vegetable organic matters and microorganisms at room temperature.

BACKGROUND OF THE INVENTION

In general, quantum energy is full of space and is the fundamental energy that enables the existence of all things.

Ore fusion fiber, which has been one of the aspirations of the textile industry worldwide, has not yet been developed due to the heavy and cold nature of the ore.

In recent years, the quantum energy ceramic powder developed by applying a special method can be uniformly dispersed and fused with a fiber raw material by converting the heavy and cold properties of the powder into lighter and warmer properties than cotton by heating, ripening, and fermentation processes.

For example, the ore is heated at a high temperature between 800° C. and 850° C. to lower the specific gravity 6 times, and the cold properties of the ore are changed to warm, then ripened and fermented to prepare a powder.

It is confirmed that the quantum energy ceramic powder fused fibers as described above attracts quantum energy in space by energy action for life support of fused ultra-high heat resistance extreme microorganisms and releases beneficial energy to human body, and thus the fiber has excellent properties such as heat generation (keep body temperature warm in winter), self-coolness (keep body temperature cool in summer), contact warmth, aeration, antibacterial activity, improved blood circulation, deodorization, flame retardancy, warmth, strength, immunoregulation and the like.

The quantum energy fused fiber is the world's best healthcare high performance fiber, because 50 supermicroorganisms and ceramic powders are fused and combined in the yarn of the fiber, so that their function is not diminished even after washing 100 times or more and thus allowing the fiber to be used semi-permanently.

Ceramic materials that emit such quantum energy are widely used, and can be used in fibers as well as various fields such as new drugs, cosmetics, polymer materials, paints, building materials, agricultural materials, sample additives, fish farming, automotive materials, electromagnetic shielding, absorbing materials, etc. In fact, it has been confirmed that they have excellent efficacy through various experiments.

DETAILED DESCRIPTION OF THE INVENTION

Problems to be Solved

The present invention has been made in view of the above points, and an object of the present invention is to provide a method for preparing a mineral ore powder using vegetable organic matters and microorganisms, wherein seven (7) mineral materials are pulverized into 325 mesh and treated for a long time at high temperature to release toxins and impurities, and then added with vegetable organic matters and microorganisms at room temperature to make mineral ore powder and dried, the toxins and impurities being discharged as gases through a water tank connected to a high temperature combustion furnace.

Solution to Solve the Problem

The present invention for achieving such an object comprises the following 4 (four) steps:

a first step of pulverizing seven (7) minerals consisting of 20% of zeolite, 10% of hornblende, 10% of elvan, 10% of illite, 10% of biotite, 20% of tourmaline and 10% of white clay into 325 mesh;

a second step of preparing a fine powder by stirring the minerals while heating at a temperature of 1,100° C. for 3 days to discharge harmful gases and impurities;

a third step of preparing a mineral ore powder by adding microorganisms and liquid or pulverized vegetable organic matters consisting of 30% of mulberry bark, 25% of pine needles, 20% of cypress, 15% of ginger plant and 15% of bush clover while adding water vapor to the minerals in which the harmful gases and impurities are discharged from the first and second steps to increase the adsorption surface coating effect; and a fourth step of drying the mineral ore powder at a temperature of 30° C. for 2 days to activate the microorganisms.

In a preferred embodiment of the present invention, the microorganisms are composed of 50% of lactic acid bacteria, 15% of antibacterial bacteria, 20% of yeast bacteria, and 15% of photosynthetic bacteria.

In another preferred embodiment of the present invention, the exothermic body is molybdenum comprising 30% of ocher, 30% of sericite, and 40% of olivine and is at a high temperature of 1,300 to 1800° C. Further, the exothermic body is configured for the hot gases to be discharged through a water tank (floc generation) after transferring the high temperature heat back to the exothermic body through the combustion furnace surrounding the exothermic body.

Effects of the Invention

The present invention removes toxins and impurities in the seven kinds of minerals that are beneficial to the human body in the interior of the exothermic body, and produces mineral ore powders to which vegetable organic matters and microorganisms are added. The powder is very excellent in properties such as heat generation, cold feeling, contact warmth, aeration, antibacterial activity, blood circulation improvement, deodorization, flame retardancy, excellent warmth, strength, immunoregulation and the like. Accordingly, the present invention provides a ceramic fusion-composite healthcare multifunctional fiber; and advanced new materials in the field of chemistry, eco-friendly green energy, agriculture, bio and electronics.

THE BEST MODE FOR CARRYING OUT THE INVENTION

Hereinafter, preferred embodiments according to the present invention will be described in detail with reference to the accompanying drawings.

Figure 1:
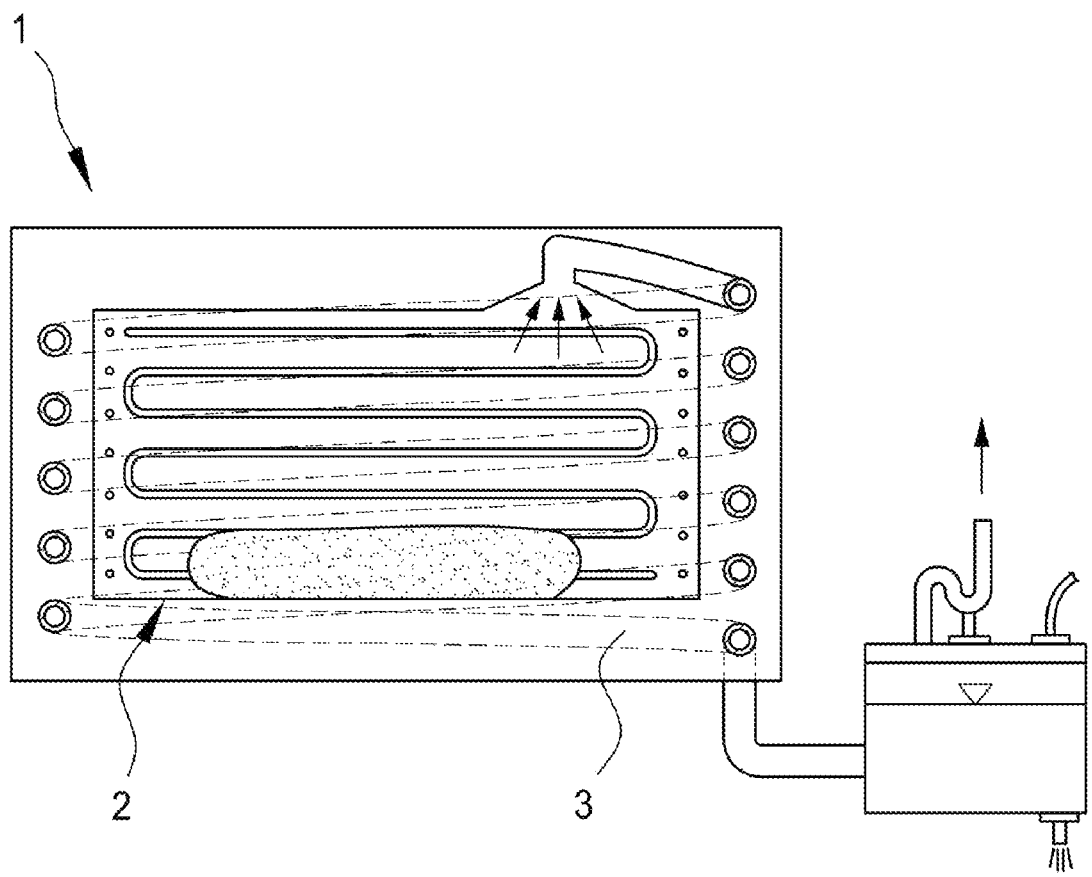
FIG. 1 is a schematic view of an exothermic body according to the present invention.
Figure 2:
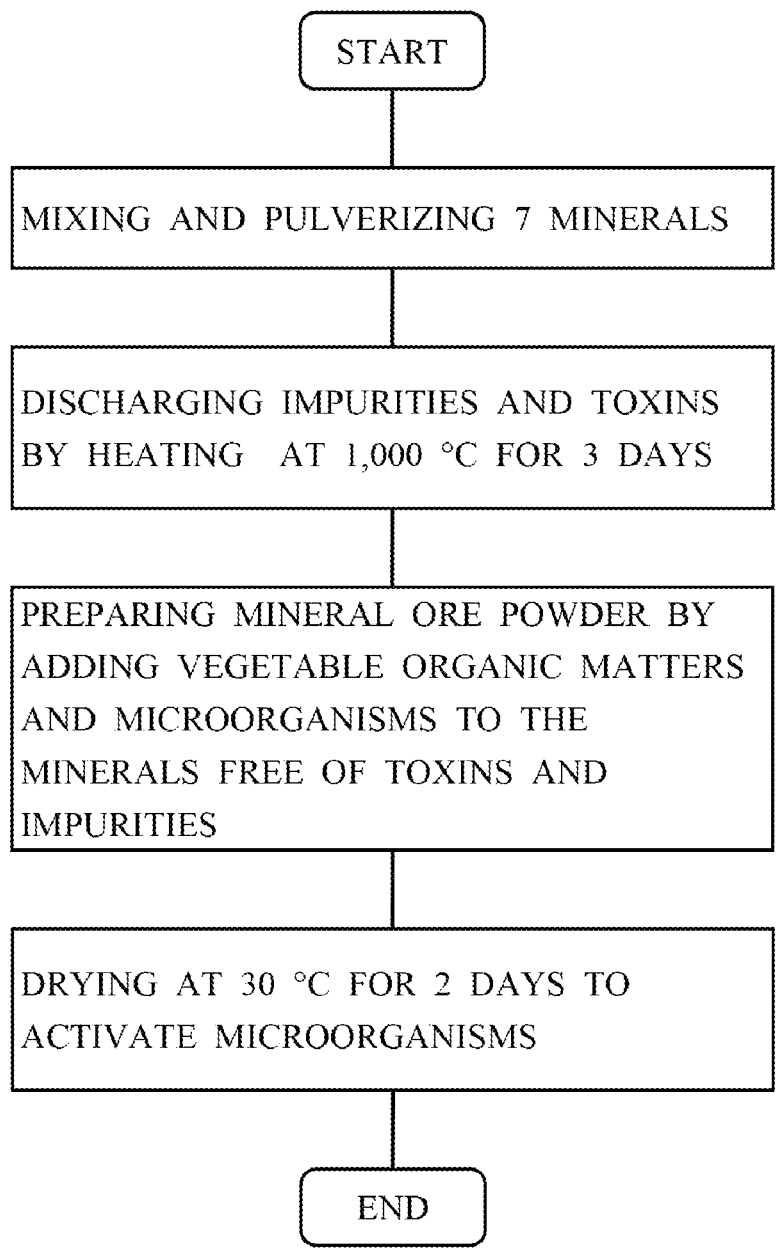
FIG. 2 is a process flow diagram of a method for preparing a mineral ore powder according to the present invention.

FIG. 1 shows an exothermic body 1 of the present invention. The exothermic body 1 is composed of 30% of ocher, 30% of sericite, and 40% of olivine. The inside of the exothermic body is provided with an inner furnace 2 for generating a high temperature, and the combustion furnace 3 is wound around the outer side of the exothermic body 1.

The combustion furnace 3 is configured to surround the outside of the exothermic body 1, so that the high temperature water vapor generated in the inner furnace 2 once again supplies the high temperature heat to the outside of the exothermic body 1 through the combustion furnace 3 surrounding the outside of the exothermic body 1, and then discharge the gases through a water tank (floc generation).

Hereinafter, the method for preparing the mineral ore powder according to the present invention is described.

First, seven minerals composed of 20% of zeolite, 10% of hornblende, 10% of elvan, 10% of illite, 10% of biotite, 20% of tourmaline and 10% of white clay are pulverized to 325 mesh.

This pulverization reduces the specific gravity of the mineral and allow the cold ore to change warmly.

And, the harmful gases and impurities contained in the minerals are ejected while heating at a temperature of 1,000° C. to 1,100° C. for 3 days.

In addition, the microorganisms and the vegetable organic matters in the form of liquid or pulverized powder, which consists of 30% of mulberry bark, 25% of pine needles, 20% of cypress, 15% of ginger plant, and 15% of bush clover, are added to the seven minerals that have been freed of impurities and stirred while heating at high temperatures as described above to produce a mineral ore powder. At this time, water vapor is added to increase the adsorption surface coating effect.

Then, the powder is then dried for 2 days at 30° C. to activate the microorganisms.

A rectangular molybdenum high temperature exothermic body 1 as shown in FIG. 1 is used for the heating at high temperature. The exothermic body 1 forms an electric furnace of 1,300 to 1,800° C.

The exothermic body 1 is composed of 30% of ocher, 30% of cericite, and 40% of olivine, and emits a large amount of far infrared rays and wave energy to increase the high temperature heating effect of the seven minerals in exothermic body 1.

According to the present invention, the mineral ore powder is prepared by treating 7 minerals pulverized into ultrafine particles as described above in the high temperature exothermic body 1 for a long time to discharge harmful gases and impurities contained in the minerals, supplying moisture to the pure mineral ore powder to increase the adsorption performance, and adding microorganisms thereto. Therefore, space energy can be maximized because the mineral ore powder fused with microorganisms acts as an energy catalyst.

The mineral ore powder containing vegetable organic matters and microorganisms can be prepared by allowing microorganisms consisting of 50% of lactic acid bacteria, 15% of antibacterial bacteria, 20% of yeast, 15% of photosynthetic bacteria in the medium at room temperature for 3 days. The said vegetable organic matters act as a medium for the microorganisms.

The mineral ore powder prepared in this way provides ultra-high heat-resistant microbial fusion healthcare multi-functional high-tech industrial raw materials that emit quantum energy, and thus can be applied to a wide range of fields such as semiconductor, pharmaceutical product, new medicine, building materials, carbon fiber, bedding, paint, adhesive, coating, agricultural organic fertilizer, etc.

EXPLANATION OF REFERENCE NUMBER

1: exothermic body
2: internal furnace
3: combustion furnace

The invention claimed is:

1. A method for preparing mineral ore powder using vegetable organic matter and microorganisms, the method comprising the following four steps:
   a first step of pulverizing seven minerals consisting of 20 wt % of zeolite, 20 wt % of hornblende, 10 wt % of elvan, 10 wt % of illite, 10 wt % of biotite, 20 wt % of tourmaline, and 10 wt % of white clay into 325 mesh to form a mineral mixture;
   a second step of preparing a fine powder by stirring the mineral mixture while heating at a temperature of 1,100° C. in an exothermic body for 3 days to discharge harmful gases and impurities;
   a third step of preparing a mineral ore powder by adding microorganisms and pulverized vegetable organic matter consisting of 30 wt % of mulberry bark, 25 wt % of pine needles, 20 wt % of cypress, 15 wt % of ginger plant, and 10 wt % of bush clover into the fine powder while adding water vapor to the fine powder to increase adsorption surface coating effect; and
   a fourth step of drying the mineral ore powder at a temperature of 30° C. for 2 days to activate the microorganisms.

2. The method of claim 1, wherein the microorganisms 50 wt % of lactic acid bacteria, 15 wt % of antibacterial bacteria, 20 wt % of yeast bacteria, and 15 wt % of photosynthetic bacteria.

3. The method of claim 1, wherein the exothermic body comprises 30 wt % of ocher, 30 wt % of sericite, and 40 wt % of olivine, an inner furnace that generates heat is further provided inside the exothermic body, and a combustion furnace surrounds the outside of the exothermic body.

* * * * *